(12) United States Patent
Jin et al.

(10) Patent No.: US 12,427,021 B2
(45) Date of Patent: Sep. 30, 2025

(54) SPLIT-TYPE INTERVENTIONAL TRICUSPID VALVE SYSTEM CAPABLE OF ACCURATELY ANCHORING

(71) Applicant: BEIJING BALANCE MEDICAL TECHNOLOGY CO., LTD., Beijing (CN)

(72) Inventors: Lei Jin, Beijing (CN); Huanlei Huang, Beijing (CN); Zhenzhong Wang, Beijing (CN); Liyan Li, Beijing (CN); Zhihao Fan, Beijing (CN); Hong Mu, Beijing (CN); Jia Wu, Beijing (CN); Kangjian Wu, Beijing (CN)

(73) Assignee: BEIJING BALANCE MEDICAL TECHNOLOGY CO., LTD., Beijing (CN)

( * ) Notice: Subject to any disclaimer, the term of this patent is extended or adjusted under 35 U.S.C. 154(b) by 40 days.

(21) Appl. No.: 18/710,521

(22) PCT Filed: Nov. 17, 2022

(86) PCT No.: PCT/CN2022/132606
§ 371 (c)(1),
(2) Date: May 15, 2024

(87) PCT Pub. No.: WO2023/088377
PCT Pub. Date: May 25, 2023

(65) Prior Publication Data
US 2025/0041057 A1     Feb. 6, 2025

(30) Foreign Application Priority Data

Nov. 17, 2021    (CN) .......................... 202111361301.3

(51) Int. Cl.
*A61F 2/24*           (2006.01)

(52) U.S. Cl.
CPC .......... *A61F 2/2436* (2013.01); *A61F 2/2418* (2013.01); *A61F 2/2433* (2013.01);
(Continued)

(58) Field of Classification Search
CPC .............. A61F 2/2418; A61F 2250/006; A61F 2/2436; A61F 2/2433
See application file for complete search history.

(56) References Cited

U.S. PATENT DOCUMENTS

| | | |
|---|---|---|
| 2010/0217382 A1 | 8/2010 | Chau et al. |
| 2012/0101572 A1 | 4/2012 | Kovalsky et al. |

(Continued)

FOREIGN PATENT DOCUMENTS

| | | |
|---|---|---|
| CN | 104220027 | 12/2014 |
| CN | 107115162 A | 9/2017 |

(Continued)

OTHER PUBLICATIONS

First office action of prior Chinese application No. 202211460784.7 dated Jun. 21, 2023.

(Continued)

*Primary Examiner* — Suba Ganesan
(74) *Attorney, Agent, or Firm* — Outlier Patent Attorneys, PLLC

(57) ABSTRACT

The split type precisely-anchorable transcatheter tricuspid valve system comprises a split transcatheter tricuspid valve anchoring stent (10) and a transcatheter artificial biological tricuspid valve (20), wherein the shape and structure of the transcatheter tricuspid valve anchoring stent (10) are matched with the tricuspid valve real structure after the patient's image data is subjected to three-dimensional reconstruction, the transcatheter tricuspid valve anchoring stent (10) is firstly delivered to the tricuspid valve site of the patient to be released, deformed and personalized and pre- (Continued)

cise alignment with a supravalvular (40) and subvalvular (50) tissue of the patient's tricuspid valve site; the transcatheter artificial biological tricuspid valve (20) is delivered into the transcatheter tricuspid valve anchoring stent (10) to be released, and the transcatheter artificial biological tricuspid valve (20) is released and deformed and expanded to a functional state, the transcatheter tricuspid valve anchoring stent (10) is deformed again to be combined with the expanded transcatheter tricuspid valve (20), and meanwhile, the re-deformation of the transcatheter tricuspid valve anchoring stent (10) is anchored by the combination of the anchoring stent and the subvalvular (50) tissue in advance. According to the split type accurately anchored transcatheter tricuspid valve system, based on a system designed by three-dimensional reconstruction, accurate anchoring of the personalized transcatheter tricuspid valve can be realized.

21 Claims, 16 Drawing Sheets

(52) U.S. Cl.
CPC ............... *A61F 2220/0008* (2013.01); *A61F 2230/0093* (2013.01); *A61F 2250/006* (2013.01)

(56) References Cited

U.S. PATENT DOCUMENTS

| | | |
|---|---|---|
| 2014/0243964 A1 | 8/2014 | Venkatasubramanian |
| 2014/0277411 A1 | 9/2014 | Börtlein et al. |
| 2018/0338832 A1 | 11/2018 | Ganesan et al. |
| 2018/0344457 A1* | 12/2018 | Gross .................. A61F 2/2409 |
| 2019/0110893 A1 | 4/2019 | Haarer et al. |
| 2021/0154010 A1 | 5/2021 | Schneider et al. |

FOREIGN PATENT DOCUMENTS

| | | |
|---|---|---|
| CN | 107613907 A | 1/2018 |
| CN | 107787209 A | 3/2018 |
| CN | 209091745 U | 7/2019 |
| CN | 113473947 A | 10/2021 |

OTHER PUBLICATIONS

First Search Report of prior Chinese application No. 202211460784.7.

International Search Report of PCT/CN2022/132606 dated Feb. 8, 2023.

* cited by examiner

SPLIT-TYPE INTERVENTIONAL TRICUSPID VALVE SYSTEM CAPABLE OF ACCURATELY ANCHORING

CROSS-REFERENCE TO RELATED APPLICATIONS

This application claims priority to International Application No. PCT/CN2022/132606, filed on Nov. 17, 2022, which claims the priority benefit of China Patent Application No. 202111361301.3, filed on Nov. 17, 2021. The contents of the above identified applications are incorporated herein by reference in their entirety.

TECHNICAL FIELD

The invention relates to an artificial biological heart valve, in particular to a split type precisely-anchorable transcatheter tricuspid valve system.

BACKGROUND ART

The tricuspid valve serves as a one-way valve for the blood to flow back to the first inlet of the heart, often experiences regurgitation (TR) due to valve dysfunction, mainly resulting in secondary lesions, it is commonly caused by valve lesions in other valve sites, if the condition continues to worsen and cannot be treated in a timely manner, a large amount of reflux can lead to heart failure or even death. Compared with the left mitral valve and aortic valve, the research and treatment of the right tricuspid valve and pulmonary valve have been overlooked in the past, and their harm has been underestimated. In recent years, the number of cases for surgical tricuspid valve repair and replacement increases year by year. For elderly patients with multiple underlying diseases, surgical valve replacement not only carries high risks but also often fails to achieve satisfactory treatment outcomes. Due to the large number of TR patients in China who have to be treated, with the effective treatment of transcatheter aortic valve (TAVR) in elderly or high-risk patients undergoing traditional surgical aortic valve replacement, there has been significant progress in the research of transcatheter tricuspid valve repair and replacement instruments in the past decade. Among them, transcatheter tricuspid replacement is considered an etiology treatment for such patients. However, due to the fact that the tricuspid valve as the intracavitary valve of the right heart, has a larger non planar elliptical and softer valve ring tissue compared to the mitral valve, mainly due to functional regurgitation, most of the valve ring has no calcification, the thinner right ventricular wall compared to the left heart, the right coronary artery adjacent to the valve ring, the more complex perivalvular environment adjacent to the conduction bundle, and the significant deformation of the valve ring and supravalvular and subvalvular with each cardiac cycle, the diversity and complexity of these anatomical forms and structures make it difficult for the transcatheter artificial biological tricuspid valve to be designed with supravalvular and perivalvular radial support, similar to aortic valves. According to the existing transcatheter tricuspid valve products and the patents disclosed in the existing similar products, from the design concept and the structural characteristics, the valve structure (FIGS. 1-2) is implanted and integrated through a catheter at one time, and it is difficult to meet the personalized complex pathological anatomical environment of the tricuspid valve site.

SUMMARY

Different from the traditional concept of transcatheter tricuspid valve product design, the invention provides a split type precisely-anchorable transcatheter tricuspid valve system. The split type meaning is that the product consists of two independent instruments of n transcatheter tricuspid valve anchoring stent and a transcatheter artificial biological tricuspid valve, the former is firstly delivered to the tricuspid valve site to be released through a catheter, and then the latter is introduced into the tricuspid valve to assist and deform in the tricuspid valve site through the balloon expandable external force, and are integrated together at the lesion site, so that personalized accurate anchoring mainly on the lesion valve tissue is realized.

Different from the structure of the traditional transcatheter tricuspid valve product, the transcatheter tricuspid valve system is composed of two parts, namely a transcatheter tricuspid valve anchoring stent and a transcatheter artificial biological tricuspid valve anchoring of the valve and the support of the valve leaflet are divided into two different structures, namely the split transcatheter tricuspid valve anchoring stent is responsible for anchoring of the valve, and the transcatheter artificial biological tricuspid valve is delivered into the pre-interventional anchoring valve frame and is combined with the stent to realize accurate anchoring.

The transcatheter tricuspid valve system of the invention comprises a split transcatheter tricuspid valve anchoring stent and a split type precisely-anchorable artificial biotricuspid valve prosthesis. One of the main contents of the present invention is that the shape and structure of the transcatheter tricuspid anchoring stent has two different anchoring states, namely a first anchoring state after being released by a catheter, and a second anchoring state after being combined with a transcatheter artificial biological tricuspid valve.

The first anchoring state is customized according to the real structure and shape of the tricuspid valve after the personalized image data of the patient is subjected to three-dimensional reconstruction and shape customization design and in-vitro three-dimensional forming processing, so that the return shape after being released through the catheter can be matched with the precise matching and alignment of the supravalvular and subvalvular tissue of the tricuspid valve site of the patient, the atrial surface of the transcatheter tricuspid valve anchoring stent is funnel-shaped to the ventricular surface, and the released form can accurately align with the supravalvular and subvalvular tissue of the tricuspid valve of the patient's dynamic lesion, and forming mutual clamping with it. The processing and shaping of the first anchoring state of the transcatheter tricuspid valve anchoring stent depends on how to achieve the precise matching degree between the transcatheter tricuspid valve anchoring stent and the real anatomical structure of the tricuspid valve of the patient. The real structure of the three-dimensional reconstruction is a digital image model or a three-dimensional printed simulation entity model; the real structure of the three-dimensional reconstruction is a three-dimensional image of a virtual simulation after digital conversion of CT, ultrasonic and nuclear magnetic integrated images and a corresponding three-dimensional printing simulation entity model.

The first anchoring state of the transcatheter tricuspid valve anchoring stent is designed and processed into an umbrella tubular stent structure according to the real anatomical morphological design of the three-tricuspid valve of the patient with three-dimensional reconstruction, that is, three parts of the atrial surface, the ventricular surface and the anchoring stent connecting part therebetween. The ① atrial surface is an umbrella shape, has an umbrella shape matched with the real form of three-dimensional reconstruction of the image data of the atrium surface of the patient, is a first lattice portion, and can be laid on the upper end of the bottom of the right atrium at the bottom of the right atrium at the bottom of the tricuspid valve; the ② ventricular surface is three positioning hook loops which are precisely preset with the boundary positions of the three leaflet leaves of the anterior leaflet, the septum and the posterior leaflet of the tricuspid valve of the patient, and after release, the anchoring stent is positioned on the atrial surface and personalized corresponding to the shape of the patient's right atrium; the ③ the connection part of the anchoring support is a funnel with a round opening and is a second lattice part. So far, it is shown that the first anchoring state of the transcatheter tricuspid valve anchoring stent refers to a personalized three-dimensional structure released from all the catheters in the catheter.

The second anchoring state of the transcatheter tricuspid valve anchoring stent refers to that in the first anchoring state, the transcatheter artificial biological tricuspid valve is delivered into the transcatheter tricuspid valve anchoring stent in the first state by the catheter, the balloon expandable external force is accompanied by the second deformation of the transcatheter tricuspid valve anchoring stent which occurs with the expansion of the transcatheter artificial biological tricuspid valve, the conical shape (funnel shape) of the original first anchoring state is deformed into the final cylindrical shape and is integrated with the expanded transcatheter artificial biological tricuspid valve, and meanwhile, the ventricular surface structure of the transcatheter tricuspid valve anchoring stent in the second anchoring state is anchored with the chordae tendineae and papillary muscle of the tricuspid valve of the patient in a precise and preset combination.

The first anchoring state of the connecting part of the transcatheter tricuspid valve anchoring stent is a three-dimensional shape-memory state of the real anatomical shape and structure of the patient after delivery and release of the catheter, the shape-memory state of the connecting part from the atrial surface to the ventricular surface has a contraction taper, the taper is 5-45 degrees, the anchoring stent connecting part is deformed and expanded to form a cylindrical second anchoring state from the conical funnel-shaped deformation of the first anchoring state depending on the shape of the lesion leaflet of the patient. In the first anchoring state of the transcatheter tricuspid valve anchoring stent, after the positioning hook loop is released through the catheter, the positioning hook loop is inserted into the junction position of the anterior leaflet, the septum and the posterior leaflet of the tricuspid valve of the patient's lesion matched with the positioning hook loop, so as to realize personalized corresponding placement of the atrial surface of a positioning anchoring stent and the right atrium of the patient. The ventricular surface of the tricuspid valve anchoring stent has a plurality of anchoring hook loops, and the anchoring hook loops extend from the connecting part to the right ventricular surface and then be folded, so as to accurately match the number of morphological contours of the real chordae tendineae and subvalvular tissue structure shape of the three-dimensional reconstruction of the subvalvular image data of the patient's lesion. The number, size, shape and folding angle of the anchoring hook loops are personalized and accurately matched with the real chordae tendineae gap, the size and shape of the tricuspid valve leaflet, and the circumferential spacing of the perivalvular tissue from the ventricular wall in three dimensions of the three-dimensional reconstruction of the subvalvular image data of the tricuspid valve of the patient's lesion.

The second anchoring state of the transcatheter tricuspid valve anchoring stent is mainly based on the three-dimensional reconstruction of the tricuspid valve leaflet shape, leaflet area, and the real anatomical structure of the chordae tendineae and papillary muscle beneath the tricuspid valve leaflet based on the patient's tricuspid valve ultrasound images, the shape, size, and bending angle of the positioning hook loop on the ventricular surface of the transcatheter tricuspid valve anchoring stent are designed and processed, so that when the transcatheter artificial biological tricuspid valve is inserted in a gripping state and pressurized and expanded by a pump, the shape and structure match an equal number of anchoring hook loops, and the positional deformation is achieved to achieve the preset final anchoring state, completing the final and accurate tight integrating with the patient's tricuspid valve site and subvalvular tissue.

The transcatheter tricuspid valve anchoring stent is characterized in that the transcatheter tricuspid valve anchoring stent is placed in a compressed state in a catheter, and is presented as a first anchoring state after being released through a catheter, and then is transformed into a second anchoring state in combination with a transcatheter artificial biological tricuspid valve, is 3 positioning hook loops of the anchoring stent connecting part, and is accurately inserted into the three interfaces of the anterior leaflet, the septum and the posterior leaflet of the tricuspid valve after being released through a catheter, so that the whole stent is positioned, the positioning hook loop not only positions the shape of the atrial surface of the transcatheter tricuspid valve anchoring stent and the shape of the right atrium of the patient and the amplitude of the systolic relaxation of the right atrium of the cardiac cycle, but also positions several anchoring hook loops of the ventricular surface of the transcatheter tricuspid valve anchoring stent in the chordae tendineae gaps under the leaflet of the tricuspid valve of the patient's lesion corresponding to the insertion, clamping, and transition of the transcatheter tricuspid valve anchoring stent to a second anchoring state, and these anchoring hook loops can be tightly intertwined and pre-set with the subvalvular tissue.

The transcatheter tricuspid valve anchoring stent is subjected to a first anchoring state after being released by a catheter and then is deformed into a second anchoring state in combination with a transcatheter artificial biological tricuspid valve, the atrial surface end portion of the connecting part of the transcatheter tricuspid valve anchoring stent is provided with a plurality of fixed support rods for embedding the transcatheter artificial biological tricuspid valve stent, and the fixed support rods are bent along the axial direction of the atrial surface and the ends thereof bend toward the axis of the anchoring stent; the connecting part of the tricuspid valve anchoring stent is provided with a plurality of end centripetal bending books for embedding the outflow end of the transcatheter artificial biological tricuspid valve stent, and the atrial surface end portions of the connecting parts of the centripetal bending hooks and the tricuspid valve anchoring stent are provided with a plurality of fixed support rods used for embedding the atrial end of the transcatheter artificial biological tricuspid valve stent in the upper and lower coaptation, and the ventricular side can be prevented from being displaced when the transcatheter artificial biological tricuspid valve is released. In the first anchoring state of the transcatheter tricuspid valve anchoring stent, the fixed support rod maintains an angle consistent with the anchoring stent connecting part, and in the second anchoring state of the tricuspid valve anchoring stent, the plurality of fixed support rods are axially parallel to the coaptation circumference, so that the end of the fixed support rod is embedded on the stent of the inflow end of the transcatheter artificial biological tricuspid valve, and structurally integrate with the transcatheter artificial biological tricuspid valve to realize zero displacement of the release of the transcatheter artificial biological tricuspid valve. The fixed support rod is 3-12, preferably 9. The first lattice portion and the second lattice portion of the transcatheter tricuspid valve anchoring stent are formed of a unit lattice composed of a compressible diamond lattice, a V-shaped lattice and/or a hexagonal or polygonal lattice, and the first lattice portion is adaptively connected to the second lattice portion. An outer periphery of the lattice portion of the atrial surface of the transcatheter tricuspid valve anchoring stent is spaced apart from the atrial wall of the patient by 1-2 mm, preferably by 1.5 mm. An inner peripheral edge diameter of the second lattice portion of the transcatheter tricuspid valve anchoring stent is matched with an outer diameter of various corresponding size specifications of the transcatheter artificial biological tricuspid valve. A surface of the transcatheter tricuspid valve anchoring stent is partially or completely coated with a layer of medical polymer film. The atrial and ventricular surfaces of the tricuspid valve anchoring stent and the connecting parts of the anchoring stent are three-dimensional shaped structures formed by laser integrated cutting or the atrial and ventricular surfaces and the connecting parts of the anchoring stent are reconnected after a split processing. The anchoring stent is a metallic material or a non-metallic material having shape-memory reshape properties. The anchoring stent is made of a nickel-titanium alloy material.

Further, the transcatheter artificial biological tricuspid valve comprises a radially compressible cobalt-chromium alloy stent which can be expanded after balloon expansion, or a radially compressible self-expanding nickel-titanium alloy stent, and three fan-shaped leaflets arranged on the inner side of the stent, any of the fan-shaped leaflets has a free edge, an arc-shaped bottom edge and leaflet boundary connecting parts extending on the two sides, and the stent is a metal net tube or a valve stent which can support three commissures of three leaflet interfaces and can be crimped. The valve stent is a cobalt-based alloy cobalt or chromium alloy or a nickel-titanium alloy. The transcatheter artificial biological tricuspid valve delivery kit comprises a transcatheter artificial biological tricuspid valve delivery device, a guide sheath, a valve holder, and a charging pump. The transcatheter tricuspid valve anchoring stent delivery device and the transcatheter artificial tricuspid valve delivery device can be delivered from the inferior vena cava via the femoral vein, or from the superior vena cava via the jugular vein or subclavian vein to the tricuspid valve site. The transcatheter tricuspid valve anchoring stent is firstly guided into the diseased tricuspid valve site of the patient through the catheter and released into the first anchoring state, and then the transcatheter artificial biological tricuspid valve is sent into the anchoring stent through the catheter, and as the valve is expanded, the transcatheter tricuspid valve anchoring stent is expanded to the second anchoring state, and meanwhile, the stent connecting part and the transcatheter artificial biological tricuspid valve are fitted and the ventricular surface of the stent completes further tight combination with the subvalvular structure to form final anchoring.

In this invention, each completion of a personalized preset transcatheter artificial biological tricuspid valve treatment process for a specific patient, all of the related data is used as an independent data unit, a large amount of personalized data is accumulated, and intelligent, large-scale and industrialization of the split type precise anchoring intervention tricuspid system is achieved through artificial intelligence.

DETAILED DESCRIPTION

By combining the accompanying drawings and the specific description of the present invention mentioned above, it is possible to have a clearer understanding of the details of the present invention. However, the specific embodiments of the present invention described herein are only for the purpose of explaining the present invention and cannot be understood in any way as a limitation of the present invention. Under the guidance of the present invention, technicians may conceive any possible variations based on the present invention, which should be considered within the scope of the present invention.

Figure 1:
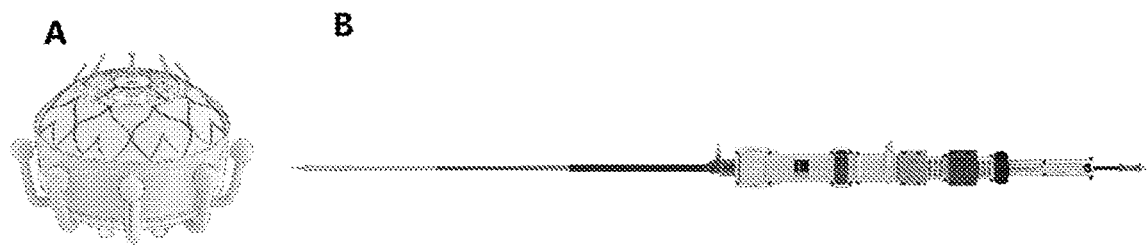
FIG. 1 shows a physical image of an EVOQUE transcatheter artificial biological tricuspid valve.
Figure 2:
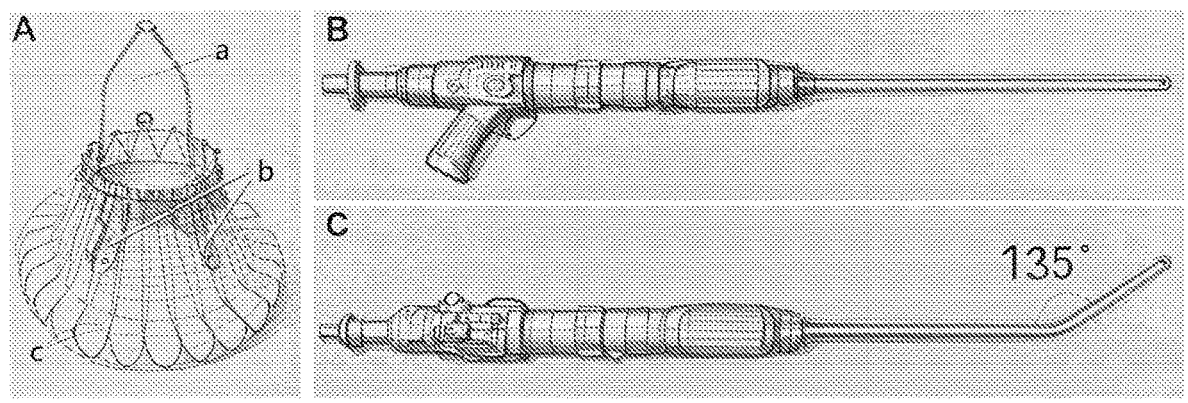
FIG. 2 shows physical image of Lux-Valve transcatheter artificial biological tricuspid valve.
Figure 3A:
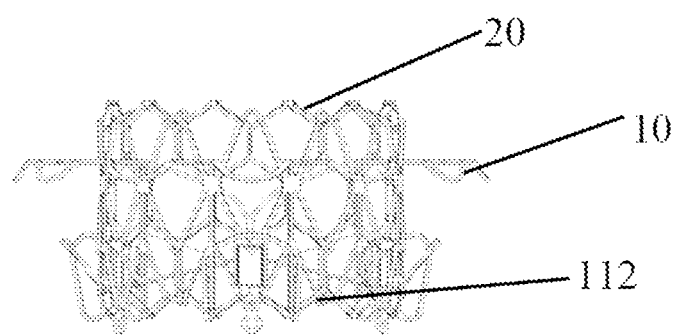
FIGS. 3A-C show a schematic diagram of a combination of a split type anchoring stent and a transcatheter artificial biological tricuspid valve with different supravalvular and subvalvular structures according to an embodiment of the present invention.
Figure 3B:
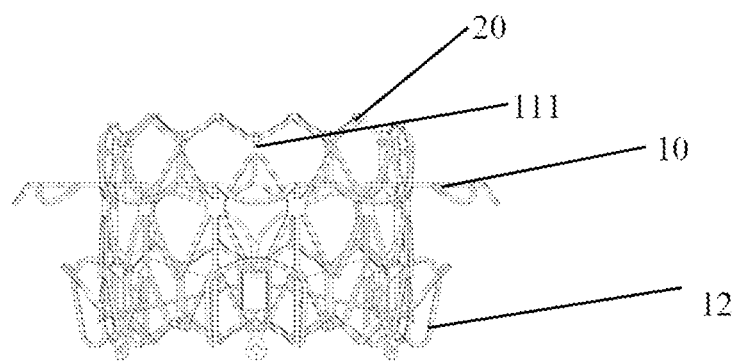
Figure 3C:
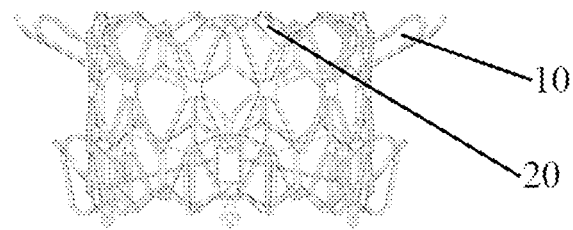

According to the present invention, the split type precisely-anchorable transcatheter tricuspid valve system comprises a split transcatheter tricuspid valve anchoring stent 10 and a transcatheter artificial biological tricuspid valve 20, the shape and structure of the transcatheter tricuspid valve anchoring stent are matched with the anatomical structure of the tricuspid valve real lesion after the patient's image data is subjected to three-dimensional reconstruction, the transcatheter tricuspid valve anchoring stent is firstly delivered to the tricuspid valve site release and deformation of the patient lesion through a catheter, and is in alignment engagement with the supravalvular 40 and subvalvular 50 tissue of the tricuspid valve site of the patient; the transcatheter artificial biological tricuspid valve is delivered into the transcatheter tricuspid valve anchoring stent which has been aligned and engaged with the tissue through a catheter, the transcatheter artificial biological tricuspid valve is released and deformed and expanded to a functional state, the transcatheter tricuspid valve anchoring stent is deformed again to be combined with the expanded transcatheter artificial biological tricuspid valve, and meanwhile, the re-deformation of the transcatheter tricuspid valve anchoring stent enables the rebinding of the anchoring stent and the tricuspid valve and subvalvular tissue of the lesion to achieve final anchoring of the transcatheter artificial biological tricuspid valve. Since the real lesion of each patient is not the same, the transcatheter tricuspid valve anchoring stent designed according to the image data of the patient through three-dimensional reconstruction is not the same, it will be adjusted according to the real situation of the patient, as shown in FIGS. 3A-C, it is a combined schematic diagram of the split type anchoring stent and the transcatheter artificial biological tricuspid valve with three types of the different supravalvular and subvalvular structures, but the general structure and constitution are based on the same design ideas and concepts.

Figure 4A:
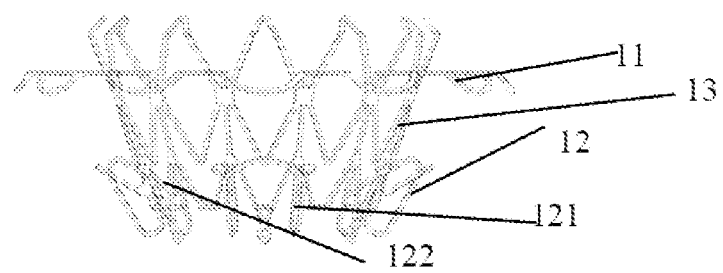
FIG. 4A-4C show a schematic diagram of a split type anchoring stent with different supravalvular and subvalvular structures according to an embodiment of the present disclosure.
Figure 4B:
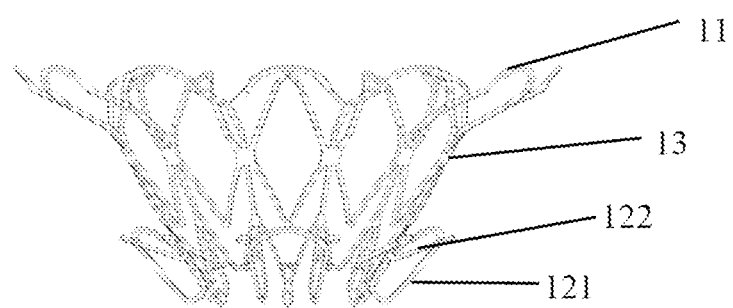
Figure 4C:
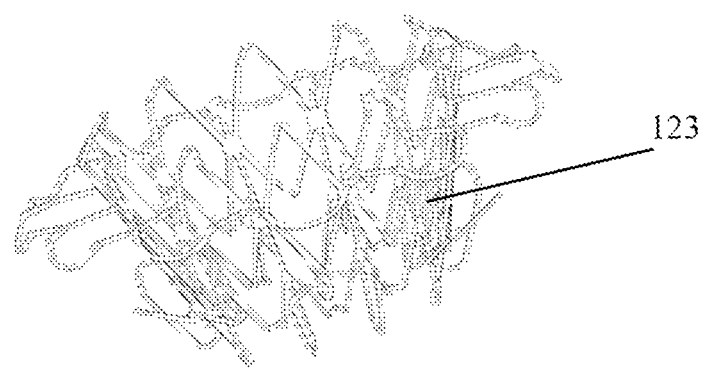
Figure 5:
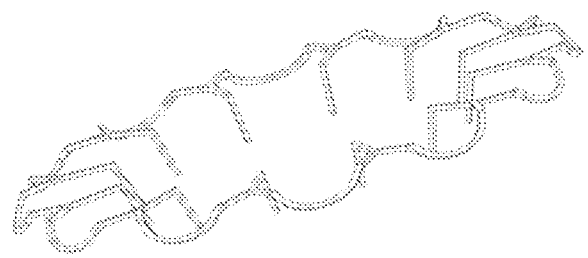
FIG. 5 shows a schematic diagram of an atrial surface of a split type anchoring stent according to an embodiment of the present disclosure.
Figure 6:
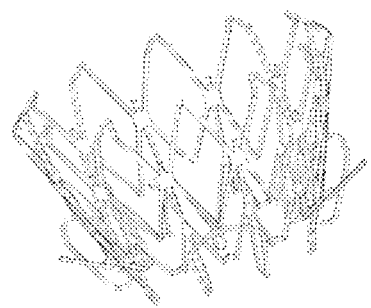
FIG. 6 shows a schematic diagram of a ventricular surface and a stent connecting part of a split type anchoring stent according to an embodiment of the present disclosure.

Referring to FIGS. 4-6, a transcatheter tricuspid valve anchoring stent 10 according to the present application, namely a funnel-shaped stent structure shaped as an atrial surface large ventricular surface, is an umbrella tubular stent structure, comprising an atrial surface 11, a ventricular surface 12 and an anchoring stent connecting part 13 therebetween, wherein the atrial surface is an umbrella sheet with an umbrella shape matched with the real shape of the three-dimensional reconstruction of the atrial surface image data of the patient, that is, the first lattice portion; the ventricular surface 12 is an anchoring hook loop 122 which is precisely preset with the three-leaflet boundary position of the anterior leaflet, the septum and the posterior leaflet of the tricuspid valve of the patient, and a plurality of anchoring hook loops 122 matched with the real shape of the three-dimensional reconstruction of the image data of the tricuspid valve of the patient; the anchoring stent connecting part 13 is a small circular opening funnel-shaped structure from the atrial surface to the ventricular surface, the length of the connecting part matches the height of the corresponding transcatheter artificial biological tricuspid valve, and has a second lattice portion which can be expanded into a cylindrical shape. As shown in FIGS. 4A-5C, the schematic diagram of the split type anchoring stent with the different supravalvular and subvalvular structures is consistent, but due to matching lesion tissues of different patients, the atrial surface 11 of different degrees of curvature, the positioning hook loop 121, and the number, angle, length and the like of the anchoring hook loop 122 are designed. In other words, the shape of the atrial surface of the transcatheter tricuspid valve anchoring stent, the size of the covering area, the shape, the number, the length and the angle and the structural relationship of the ventricular surface of the stent and the anchoring hook loop are all according to the pre-operative CT image data of the individual of the patient, after three-dimensional reconstruction (3mensio), the real structures of the atrium (supravalvular) and ventricle (subvalvular) of the patient, as well as the corresponding matching of the various diameter limit structures measured by reference to three-dimensional ultrasound images with the real dimensions, were designed, and based on this, the processing drawings of the interventional tricuspid valve anchoring stent were designed, a personalized tricuspid valve anchoring stent was finally customized through the three-dimensional laser cutting and three-dimensional forming processing of specific nickel titanium memory alloy pipes.

Figure 7A:
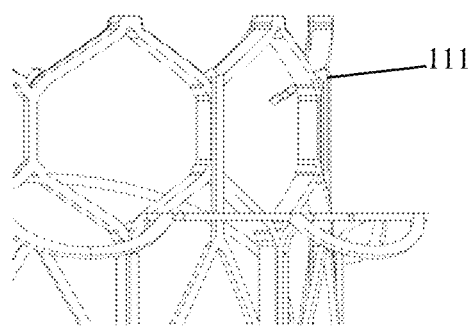
FIGS. 7A-C show a schematic diagram of fixed support rods and centripetal bending of a split type anchoring stent according to an embodiment of the present disclosure.
Figure 7B:
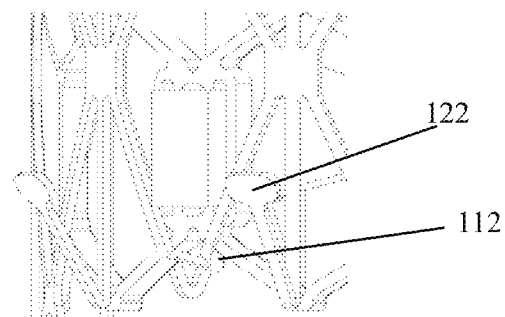
Figure 7C:
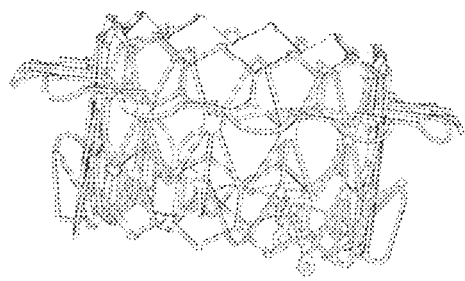

Referring to FIGS. 7A-7C, in order to make the combination of the anchoring stent and the transcatheter artificial biological tricuspid valve more firm, the end portion of the atrial surface 11 of the connecting part of the transcatheter tricuspid valve anchoring stent is provided with a plurality of fixed support rods 111 for embedding the transcatheter artificial biological tricuspid valve stent, and the end portion of the fixed support rod extending axially along the atrial surface direction is bent towards the axis of the anchoring stent. Alternatively, the connecting part of the tricuspid valve anchoring stent is provided with a plurality of end centripetal bending hooks 112 for embedding the outflow end of the transcatheter artificial biological tricuspid valve stent, and similar centripetal bending hooks can also replace the fixed support rod on the atrial surface. In the first anchoring state of the transcatheter tricuspid valve anchoring stent, the fixed support rod 111 maintains an angle consistent with the anchoring stent connecting part, and in the second anchoring state of the tricuspid valve anchoring stent, the plurality of fixed support rods 111 are axially parallel to the coaptation circumference, so that the end of the fixed support rod is embedded on the stent of the inflow end of the transcatheter artificial biological tricuspid valve, and the transcatheter artificial biological tricuspid valve is fixed to prevent displacement to the atrial surface. The fixed support rod 111 is 3-12.

The first lattice portion and the second lattice portion of the transcatheter tricuspid valve anchoring stent are formed of a unit lattice composed of a compressible diamond lattice, a V-shaped lattice and/or a hexagonal or polygonal lattice, and the first lattice portion is adaptively connected to the second lattice portion. An outer periphery of the lattice portion of the atrial surface of the transcatheter tricuspid valve anchoring stent is spaced apart from the atrial wall of the patient by 1-2 mm, preferably by 1.5 mm. An inner peripheral edge diameter of the second lattice portion of the transcatheter tricuspid valve anchoring stent is matched with an outer diameter of various corresponding size specifications of the transcatheter artificial biological tricuspid valve. A surface of the transcatheter tricuspid valve anchoring stent is partially or completely coated with a layer of medical polymer film. The atrial and ventricular surfaces of the tricuspid valve anchoring stent and the connecting parts of the anchoring stent are three-dimensional shaped structures formed by laser integrated cutting or the atrial and ventricular surfaces and the connecting parts of the anchoring stent are reconnected after a split processing. The anchoring stent is a metallic material or a non-metallic material having shape-memory reshape properties, for example, a nickel-titanium alloy material.

Figure 8A:
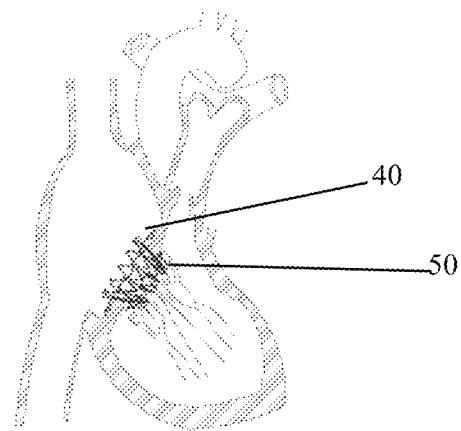
FIG. 8A-8B show a schematic diagram of a first anchoring state after a transcatheter tricuspid valve anchoring stent is implanted into a human body according to an embodiment of the present disclosure.
Figure 8B:
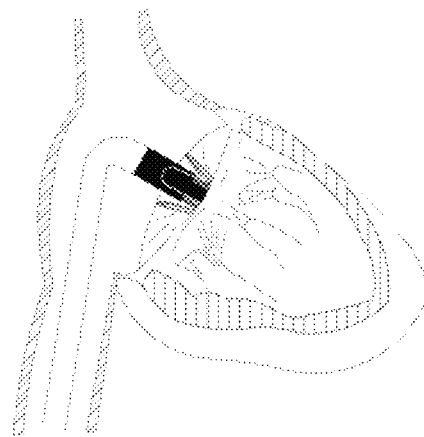
Figure 9A:
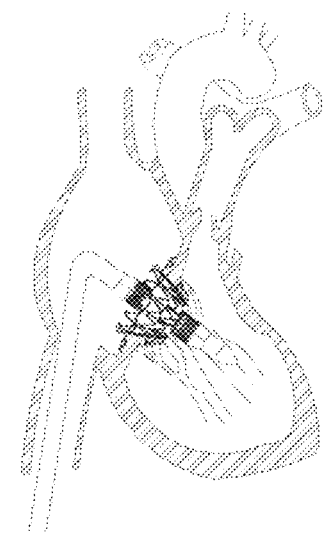
FIGS. 9A-B show a schematic diagram of a second anchoring state after a transcatheter tricuspid anchoring stent is implanted into a human body according to an embodiment of the present disclosure.
Figure 9B:
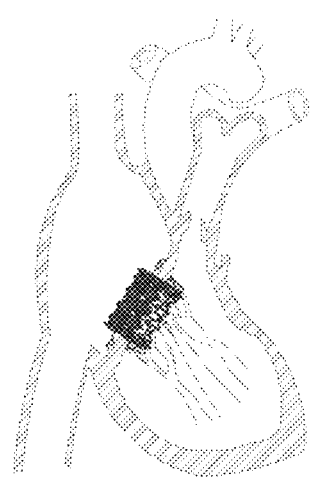
Figure 10:
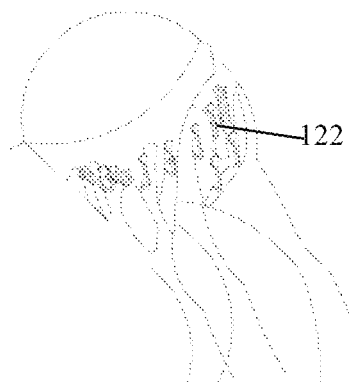
FIG. 10 shows a schematic diagram of anchoring hook loops and chordae tendineae secondary anchoring after a transcatheter tricuspid anchoring stent is implanted into a human body according to an embodiment of the present disclosure.

The above process involves manufacturing a tricuspid valve anchoring stent based on real patient imaging data as the pre grip state of the stent, which is also the first anchoring state after the stent is delivered through a catheter to the tricuspid valve and released at the site of the lesion, as shown in FIGS. 8A-8B. The second anchoring state of the transcatheter tricuspid valve anchoring stent is that when the transcatheter artificial biological tricuspid valve is delivered into the anchoring stent through the catheter, by balloon assisted expansion, the valve is expanded (or the nickel-titanium memory alloy valve stent self-expands) to deform the tricuspid valve anchoring stent from the first anchoring state to the second anchoring state, and the deformation force of the stent is combined with the balloon expandable force released by the transcatheter artificial biological tricuspid valve as a whole as shown in FIGS. 9A-9B. And meanwhile, the anchoring stent ventricular surface anchoring hook loop of the chordae tendineae under the alignment insertion valve and the subvalvular tissue, under the action of the transcatheter artificial biological tricuspid valve balloon expandable external force, as the anchoring stent is deformed from the first anchoring state to the second anchoring state, the ventricular surface anchoring hook loop is further tightly combined with the chordae tendineae and the subvalvular tissue 50 to achieve final anchoring, as shown in FIG. 10. At the same time, in the first anchoring state of the anchoring stent, the atrial end fixed support rod or stent bending of the connecting structure of the anchoring stent is deformed into a second anchoring state, and the anchoring stent is axially parallel to the encircling circumference, so that the fixed support rod end or stent bending and the connecting ventricular end of the stent hook back force buckle onto the support rod inserted at both ends of the tricuspid valve stent, and this anchoring stent and the automatic interlocking structure at both ends of the transcatheter artificial biological tricuspid valve stent precisely combine the valve and the anchoring stent to ensure zero displacement of the transcatheter artificial biological tricuspid valve, as shown in FIGS. 7A-7B.

Figure 11A:
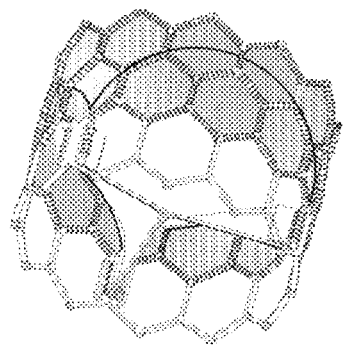
FIG. 11A-11B show a schematic diagram of a transcatheter artificial biological tricuspid valve before and after compression according to an embodiment of the present disclosure.
Figure 11B:
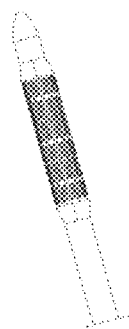
Figure 12:
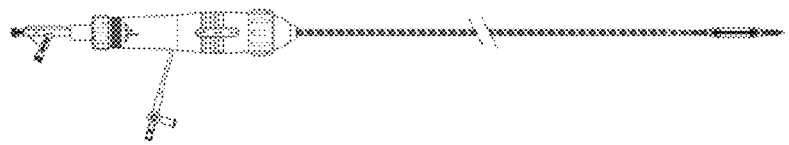
FIG. 12 shows a schematic diagram of a delivery system according to an embodiment of the present disclosure.

The core point of the invention is as follows: ① the split anchoring stent is designed and the transcatheter artificial biological tricuspid valve is delivered through catheters before and after intervention, and combined in the heart; ② according to the image data of the preoperative lesion tricuspid valve flap and the lower leaflet structure of the patient, the anchoring stent structure is designed in a personalized way and is shaped in three dimensions based on the image data of the supravalvular and subvalvular structure of the tricuspid valve of the patient's preoperative lesion; ③ by utilizing the valve leaflet junction and using a specially designed positioning hook loop, accurately locate the atrial surface shape similarity of the anchoring stent, and align the subvalvular hook loop structure with the chordae tendineae and papillary muscle of the tricuspid valve leaflet; ④ after the release of the anchoring stent, the first anchoring state (funnel-shaped) is determined based on the patient's real pathological anatomical structure, determining the principle and location of the final anchoring, that is, the preset transition state of the second anchoring state (cylindrical), aligning with the personalized pathological anatomical structure, and then, with the help of the deformation force released by the balloon expansion of the tricuspid valve, the anchoring stent is deformed into the second anchoring state of the anchoring stent, so that the transcatheter artificial biological tricuspid valve and the anchoring stent are integrated into a second anchoring state in the heart, and then the clamping is achieved under the supravalvular valve, so that the subvalvular tissue is twisted again between the anchoring stent and the ventricular wall, completing the final anchoring; ⑤ the anchoring stent is deformed from the first state to the second state, the deformation process achieves automatic binding with the transcatheter artificial biological tricuspid valve, and the release manipulation of the transcatheter artificial biological tricuspid valve can be automatically and accurately achieved.

the transcatheter artificial biological tricuspid valve disclosed by the invention, due to the combination of anchoring stent, only serves the reasonable support of the tricuspid valve, the transcatheter artificial biological tricuspid valve comprises a radially compressible cobalt-chromium alloy stent which can be expanded after balloon expansion, or a radially compressible self-expanding nickel-titanium alloy stent, and three fan-shaped leaflets arranged on the inner side of the stent, any of the fan-shaped leaflets has a free edge, an arc-shaped bottom edge and leaflet boundary connecting parts extending on the two sides, and the stent is a metal net tube or a valve stent which can support three commissures of three leaflet interfaces and can be crimped. The valve frame is a cobalt-based alloy cobalt or chromium alloy or a nickel-titanium alloy. Please refer to FIGS. 11A-11B.

The tricuspid valve system of the present application further includes a delivery assembly 30, the delivery assembly comprises a transcatheter tricuspid valve anchoring stent delivery set 31 and a transcatheter artificial biological tricuspid valve delivery set 32. The transcatheter artificial biological tricuspid valve delivery kit comprises a transcatheter artificial biological tricuspid valve delivery device, a guide sheath, a valve holder, and a charging pump. The transcatheter tricuspid anchoring stent delivery device and the transcatheter artificial biological tricuspid valve delivery device are accessible via femoral vein puncture, apical puncture, or left atrial puncture. These techniques are similar to the prior art.

When using the transcatheter tricuspid valve system in this application for interventional treatment, it is necessary to enter through the inferior vena cava via the femoral vein or the superior vena cava via the jugular vein.

Figure 13:
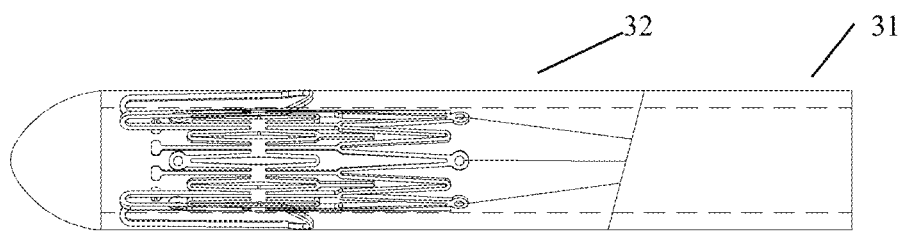
FIG. 13 shows a schematic diagram of a loading of a transcatheter tricuspid valve anchoring stent through atrial septum by a transfemoral approach according to an embodiment of the present invention.

FIGS. 13-5 show the transfemoral approach from inferior vena cava.

Figure 14A:
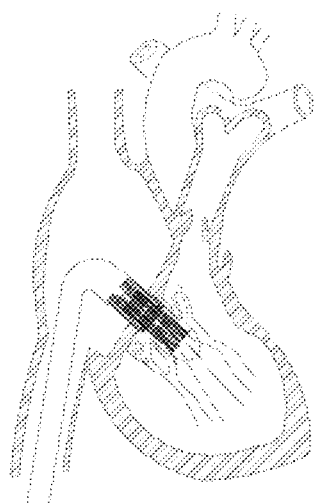
FIG. 14A-D show a schematic diagram of a process of a transcatheter tricuspid valve anchoring stent through atrial septum by a transfemoral approach according to an embodiment of the present invention.
Figure 14B:
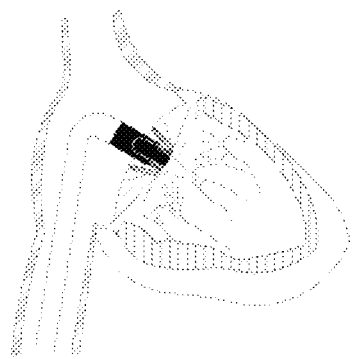
Figure 14C:
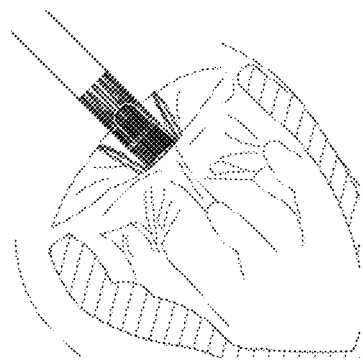
Figure 14D:
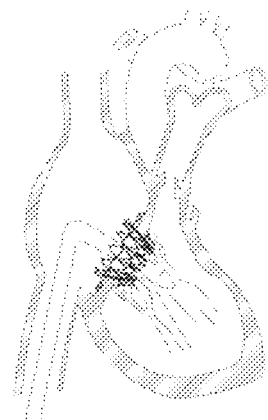
Figure 15A:
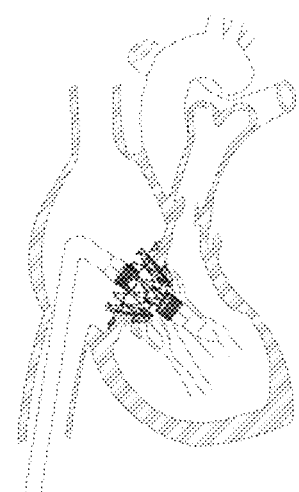
FIG. 15A-B show a schematic diagram of a process of feeding a transcatheter artificial biological tricuspid valve through atrial septum into an anchoring stent by a transfemoral approach according to an embodiment of the present invention.
Figure 15B:
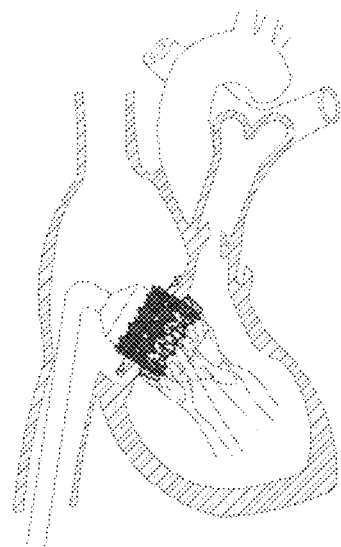

The transfemoral approach from inferior vena cava is the most commonly used and convenient approach. The loaded anchoring stent is delivered into the tricuspid valve of the lesion of the right atrium patient through the transfemoral approach from the inferior vena cava (FIG. 14A), the positioning hook loop is released to complete positioning (FIG. 14B), the anchoring stent is sequentially released on the ventricular surface (FIG. 14C), and the ventricular surface anchoring hook loop is aligned and combined, that is, the anchoring stent is in the first anchoring state (FIG. 14D); the anchoring stent delivery device is withdrawn, the loaded transcatheter artificial biological tricuspid valve is delivered into the anchoring stent along the original path (FIG. 15A), then the transcatheter artificial biological tricuspid valve is assisted by balloon assistance, the anchoring stent is deformed into the second anchoring state, the anchoring stent is automatically and accurately combined with the transcatheter artificial biological tricuspid valve, and meanwhile, the anchoring stent is clamped with the inferior tissue to complete final anchoring (FIG. 15B).

Figure 16A:
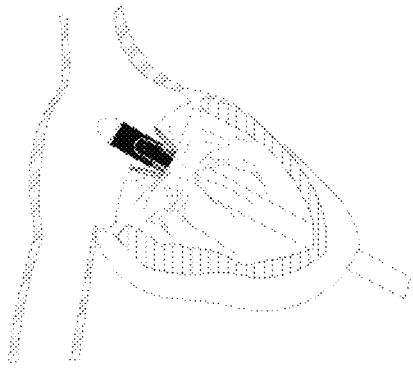
FIGS. 16A-C show a schematic diagram of a process of introducing a composite approach into a transcatheter tricuspid valve anchoring stent according to an embodiment of the present invention.
Figure 16B:
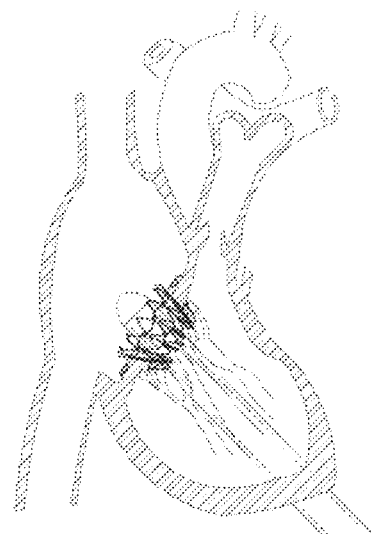
Figure 16C:
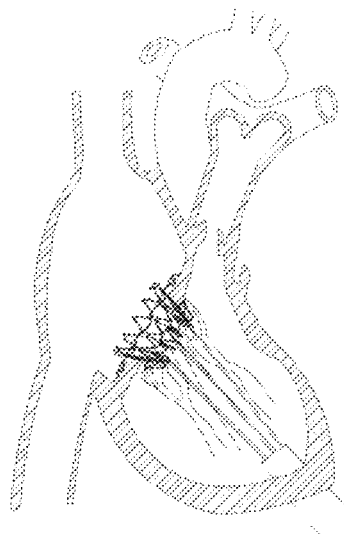
Figure 17A:
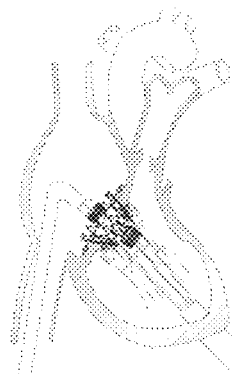
FIGS. 17A-D show a schematic views of a process of feeding a transcatheter artificial biological tricuspid valve into an anchoring stent via a composite approach according to an embodiment of the present invention.
Figure 17B:
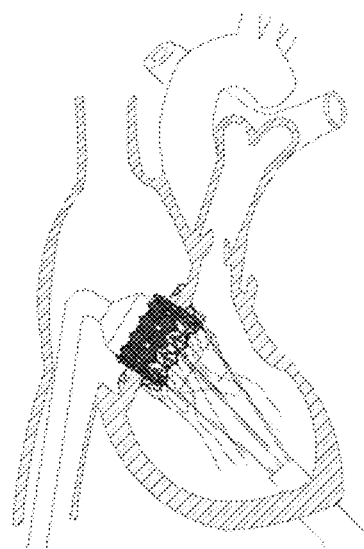
Figure 17C:
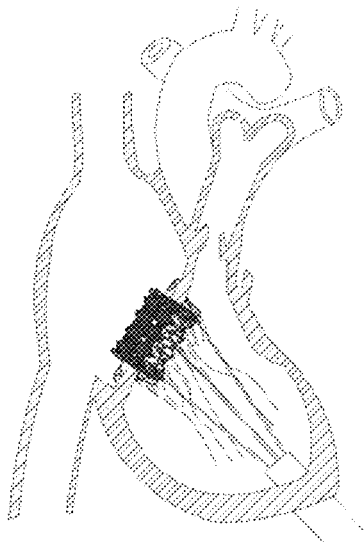
Figure 17D:
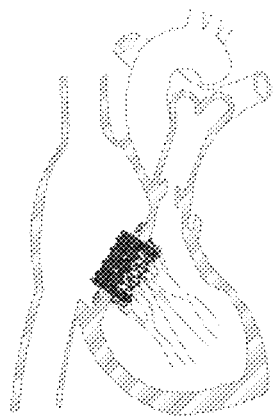

The transcatheter tricuspid valve system of the present application also passes through a jugular vein approach, as shown in FIG. 16-17.

The loaded anchoring stent is delivered into the tricuspid valve of the lesion of the right atrium patient from the superior vena cava through the jugular vein, and the following procedure is the same (FIGS. 16-17).

The above embodiments are only intended to fully illustrate the normative embodiments of the present invention. The intervention tricuspid valve system of the present invention has been experimentally implemented in animals and confirmed to be feasible.

The invention can realize the significance that: ① the split design realizes that the valve leaflet support and the valve anchoring are separated in function, the anchoring of the valve to the tricuspid valve position is delivered to the anchoring stent, so that the anchoring personalized design can be realized, and meanwhile, the anchoring stent and the transcatheter valve are inserted step by step, so that can avoid the difficulties in catheter delivery caused by the volume is too large after crimping; ② the anchoring principle and the pre-design and measurement of the final anchoring part are carried out through the anatomical structure characteristics of the lesion valve, and the second anchoring state of the anchoring stent is determined; the size and dimension of each part are constructed through the personalized image data of the patient, the special software and the three-dimensional printing pretest to complete the preset transition state, namely the three-dimensional shaping design and processing of the first anchoring state, so that the catheter is accurately aligned after being released, and the support is provided for smooth delivery of the transcatheter valve. For example, the conical structure of the first state of the anchoring stent can be moderately expanded and narrow, and can also be constrained more severely; the former not only provides a channel for valve intervention, but also can avoid sudden expansion of the stenotic lesion; the former can relieve a large amount of regurgitation of the valve insufficiency, and provides space and time guarantee for the entry of the transcatheter artificial biological tricuspid valve; ③ the external force released by the valve is used for driving the anchoring support to be deformed into a cylindrical second state from the funnel-like first anchoring state, and the deformation generates an anchoring stent centripetal gripping valve, so that the zero displacement of the valve is ensured by fitting with the transcatheter valve, and the anchoring hook loop structure is further tightly combined with the lower leaflet tissue by means of the ventricular surface anchoring hook loop structure, so that the pre-designed alignment anchoring is completed, and meanwhile, clamping is formed on the anchoring stent and the structure on the valve to achieve final anchoring; ④ the arrangement support rod structure of the inflow end and the outflow end of the connecting part of the transcatheter tricuspid valve anchoring stent can be integrated with the transcatheter artificial biological tricuspid valve from both ends to ensure that the valve is not displaced; ⑤ in the split type precisely-anchorable transcatheter tricuspid valve system described above, each completion of the transcatheter artificial biological tricuspid valve treatment process accurately anchored for the personalized preset realization, the analysis of related data, the shape design of the transcatheter tricuspid valve anchoring stent, processing and manufacturing, related data obtained in the whole process of interventional treatment and postoperative follow-up visit data and the like, as an independent data unit, a large amount of personalized image data, an anchoring stent design and related data such as processing and manufacturing parameters, a interventional treatment process and a postoperative result are accumulated, and the intelligent, commercialization and large-scale application of the interventional treatment implementation of the split type precisely-anchorable transcatheter tricuspid valve system is gradually realized.

The invention claimed is:

1. A split type precisely-anchorable transcatheter tricuspid valve system, characterized in that, the system comprises a split transcatheter tricuspid valve anchoring stent and a transcatheter artificial biological tricuspid valve, wherein the transcatheter tricuspid valve anchoring stent has a shape which is be matched with a human's tricuspid valve obtained by three-dimensional reconstruction of the tricuspid valve's image data, when the system is used, the transcatheter tricuspid valve anchoring stent is configured to be delivered to the tricuspid valve's site to be released, deformed and precisely aligned with a supravalvular tissue and subvalvular tissue at the tricuspid valve's site;

the transcatheter artificial biological tricuspid valve is configured to be delivered into the transcatheter tricuspid valve anchoring stent to be released, deformed and expanded, the transcatheter tricuspid valve anchoring stent is configured to be re-deformed to be combined with the expanded transcatheter artificial biological tricuspid valve, so as to combine the anchoring stent and the subvalvular tissue;

the transcatheter tricuspid valve anchoring stent is an umbrella tubular stent structure, comprising an atrial surface, a ventricular surface and an anchoring stent connecting part therebetween, wherein the atrial surface has a first lattice portion which is an umbrella sheet having an umbrella shape matched with human's atrial surface obtained by three-dimensional reconstruction of image data;

the ventricular surface is three positioning hook loops which are precisely preset with the boundary positions of the anterior leaflet, the septum and the posterior leaflet of the tricuspid valve; and the anchoring stent connecting part has a second lattice portion which is a circular funnel shape having a circular opening diameter which is matched with an inner diameter of the tricuspid valve's rings and an outer diameter of the transcatheter artificial biological tricuspid valve, and a lower opening of the funnel is matched with a shape of tricuspid valve stenosis and/or regurgitation lesions;

the atrial surface's end portions are provided with a plurality of fixed support rods for embedding the transcatheter tricuspid valve anchoring stent, and the fixed support rods are extended along an axial direction of the atrial surface and the ends thereof are bent toward an axis of the transcatheter tricuspid valve anchoring stent.

2. The split type precisely-anchorable transcatheter tricuspid valve system according to claim 1, characterized in that, the tricuspid valve system further comprises a delivery assembly, the delivery assembly comprises a transcatheter tricuspid valve anchoring stent delivery set and a transcatheter artificial biological tricuspid valve delivery set, and the transcatheter tricuspid valve anchoring stent delivery set comprises a delivery catheter, a transcatheter tricuspid valve anchoring stent delivery device and a stent loader.

3. The split type precisely-anchorable transcatheter tricuspid valve system according to claim 2, characterized in that, the transcatheter artificial biological tricuspid valve delivery kit comprises a transcatheter artificial biological tricuspid valve delivery device, a guide sheath, a valve holder, and a charging pump.

4. The split type precisely-anchorable transcatheter tricuspid valve system according to claim 3, characterized in that, the transcatheter tricuspid valve anchoring stent delivery device and the transcatheter artificial tricuspid valve delivery device can be delivered from the inferior vena cava via the femoral vein, or from the superior vena cava via the jugular vein or subclavian vein at the tricuspid valve's site.

5. The split type precisely-anchorable transcatheter tricuspid valve system according to claim 1, characterized in that, the transcatheter tricuspid valve anchoring stent has a compressed state disposed in the catheter, a first anchoring state after being released via the catheter, and a second anchoring state after being combined with the transcatheter artificial biological tricuspid valve,
  in the first anchoring state, the tricuspid valve anchoring stent is configured to be released via the catheter and deformed to be precisely aligned and combined with the supravalvular tissue and the subvalvular tissue at the tricuspid valve's site;
  in the second anchoring state, the transcatheter artificial biological tricuspid valve is configured to be delivered by the catheter into the transcatheter tricuspid valve anchoring stent which has been in the first state and expanded by balloon expandable external force so as to cause a secondary deformation, and the tricuspid valve anchoring stent is configured to be integrated with the expanded transcatheter artificial biological tricuspid valve, so as to be combined with the leaflet or the subvalvular tissue at the tricuspid valve's site.

6. The split type precisely-anchorable transcatheter tricuspid valve system according to claim 5, characterized in that,
  in the first anchoring state, the transcatheter tricuspid valve anchoring stent is processed and shaped into a funnel shape with a large atrial surface and a small ventricular surface, and the deformation and return of the transcatheter tricuspid valve anchoring stent after being delivered and released through a catheter adapt to be combined with the supravalvular tissue and the subvalvular tissue of the tricuspid valve;
  in the second anchoring state, the transcatheter tricuspid valve anchoring stent in the first anchoring state and the transcatheter artificial biological tricuspid valve which has been delivered into the stent via the catheter are configured to be expanded by balloon and integrated together, so that the transcatheter tricuspid valve anchoring stent is deformed from a funnel shape into a cylindrical shape together with the transcatheter artificial biological tricuspid valve, which generates a centripetal return clip so as to be combined with the subvalvular tissue at the tricuspid valve's site.

7. The split type precisely-anchorable transcatheter tricuspid valve system according to claim 1, characterized in that, the ventricular surface of the tricuspid valve anchoring stent has a plurality of anchoring hook loops which are extended and folded from the anchoring stent connecting part to the right ventricular surface, the anchoring hook loops are configured to be matched with morphological contours of human's chordae tendineae and the subvalvular tissue obtained by three-dimensional reconstruction of subvalvular image data.

8. The split type precisely-anchorable transcatheter tricuspid valve system according to claim 7, characterized in that, the anchoring hook loops are divided into 3 groups corresponding to three leaflets, and in each group, there are 3-9 anchoring hook loops which corresponds to the number of chordae tendineae and chordae tendineae gaps.

9. The split type precisely-anchorable transcatheter tricuspid valve system according to claim 1, characterized in that, the anchoring stent connecting part is provided with a plurality of centripetal bending hooks for embedding the outflow ends of the transcatheter tricuspid valve anchoring stent, and the centripetal bending hooks centripetally surround an lower part of the transcatheter tricuspid valve anchoring stent, configured to fix the transcatheter artificial biological tricuspid valve so as to prevent it from moving towards the atrial surface.

10. The split type precisely-anchorable transcatheter tricuspid valve system according to claim 1, characterized in that,
  in the first anchoring state of the transcatheter tricuspid valve anchoring stent, the fixed support rods maintain an angle consistent with the anchoring stent connecting part, and
  in the second anchoring state of the tricuspid valve anchoring stent, the fixed support rods are axially parallel and centripetally surround an upper part of the transcatheter tricuspid valve anchoring stent, ends of the fixed support rods are embedded on the inflow ends of the transcatheter tricuspid valve anchoring stent, making the transcatheter tricuspid valve anchoring stent structurally integrated with the transcatheter artificial biological tricuspid valve so as to prevent the transcatheter artificial biological tricuspid valve from moving during the releasing.

11. The split type precisely-anchorable transcatheter tricuspid valve system according to claim 1, characterized in that, the number of the fixed support rods is 3-12.

12. The split type precisely-anchorable transcatheter tricuspid valve system according to claim 1, characterized in that, the first lattice portion and the second lattice portion of the transcatheter tricuspid valve anchoring stent are formed of a unit lattice composed of a compressible diamond lattice, a V-shaped lattice and/or a hexagonal or polygonal lattice, and the first lattice portion is adaptively connected to the second lattice portion.

13. The split type precisely-anchorable transcatheter tricuspid valve system according to claim 1, characterized in that, an outer periphery of the first lattice portion of the atrial surface of the transcatheter tricuspid valve anchoring stent is spaced apart from an atrial wall by 1-2 mm.

14. The split type precisely-anchorable transcatheter tricuspid valve system according to claim 1, characterized in that, an inner peripheral edge diameter of the second lattice portion of the transcatheter tricuspid valve anchoring stent is matched with an outer diameter of the transcatheter artificial biological tricuspid valve.

15. The split type precisely-anchorable transcatheter tricuspid valve system according to claim 1, characterized in that, a surface of the transcatheter tricuspid valve anchoring stent is partially or completely coated with a layer of medical polymer film.

16. The split type precisely-anchorable transcatheter tricuspid valve system according to claim 1, characterized in that, the atrial and ventricular surfaces of the tricuspid valve anchoring stent and the anchoring stent connecting parts are three-dimensional shaped structures formed by laser integrated cutting or the atrial and ventricular surfaces and the anchoring stent connecting parts are reconnected after a split processing.

17. The split type precisely-anchorable transcatheter tricuspid valve system according to claim 1, characterized in that, the anchoring stent is a metallic material or a non-metallic material having shape-memory reshape properties.

18. The split type precisely-anchorable transcatheter tricuspid valve system according to claim 1, characterized in that, the anchoring stent is made of a nickel-titanium alloy material.

19. The split type precisely-anchorable transcatheter tricuspid valve system according to claim 1, characterized in that, the transcatheter artificial biological tricuspid valve comprises a radially compressible cobalt-chromium alloy stent which can be expanded after balloon expansion, or a radially compressible self-expanding nickel-titanium alloy stent, and three fan-shaped leaflets arranged on the inner side of the stent, any of the fan-shaped leaflets has a free edge, an arc-shaped bottom edge and leaflet boundary connecting parts extending on the two sides, and the stent is a metal net tube or a valve stent which can support three commissures of three leaflet interfaces and can be crimped.

20. The split type precisely-anchorable transcatheter tricuspid valve system according to claim 19, characterized in that, the valve stent is a cobalt-based alloy cobalt or chromium alloy or a nickel-titanium alloy.

21. The split type precisely-anchorable transcatheter tricuspid valve system according to claim 19, characterized in that, the transcatheter tricuspid valve anchoring stent is configured to be guided into a diseased tricuspid valve's site through the catheter and released into the first anchoring state, and the transcatheter artificial biological tricuspid valve is configured to be sent into the anchoring stent through the catheter, and as the transcatheter artificial biological tricuspid valve is expanded, the transcatheter tricuspid valve anchoring stent is configured to be expanded to the second anchoring state, so as to fit the anchoring stent connecting part and the transcatheter artificial biological tricuspid valve and combine the ventricular surface of the stent with the subvalvular structure to form final anchoring.

* * * * *